United States Patent
Lopes

(10) Patent No.: US 9,603,677 B2
(45) Date of Patent: Mar. 28, 2017

(54) PRE-FABRICATED LIGATURE WITH VARIABLE FRICTION

(76) Inventor: Alexandre Gallo Lopes, Ribeirao Preto (BR)

( * ) Notice: Subject to any disclaimer, the term of this patent is extended or adjusted under 35 U.S.C. 154(b) by 0 days.

(21) Appl. No.: 13/816,474

(22) PCT Filed: Aug. 11, 2011

(86) PCT No.: PCT/BR2011/000271
§ 371 (c)(1),
(2), (4) Date: Apr. 15, 2013

(87) PCT Pub. No.: WO2012/019262
PCT Pub. Date: Feb. 16, 2012

(65) Prior Publication Data
US 2013/0266907 A1    Oct. 10, 2013

(30) Foreign Application Priority Data
Aug. 11, 2010 (BR) .................................. 9001529 U

(51) Int. Cl.
*A61C 7/28* (2006.01)
*A61C 7/30* (2006.01)

(52) U.S. Cl.
CPC ............... *A61C 7/28* (2013.01); *A61C 7/303* (2013.01)

(58) Field of Classification Search
CPC .............. A61C 7/30; A61C 7/28; A61C 7/303
USPC ...................................... 433/10–15
See application file for complete search history.

(56) References Cited

U.S. PATENT DOCUMENTS

| 2,548,864 | A | * | 4/1951 | Brusse ............................ 433/11 |
| 2,665,480 | A | * | 1/1954 | Johnson .................... A61C 7/12 433/11 |
| 3,775,850 | A | * | 12/1973 | Northcutt ............... A61C 7/143 433/16 |
| 3,871,096 | A | * | 3/1975 | Wallshein ............... A61C 7/30 433/11 |
| 4,149,314 | A | * | 4/1979 | Nonnenmann ........ A61C 7/285 433/13 |
| 4,260,375 | A | * | 4/1981 | Wallshein ...................... 433/11 |
| 4,373,914 | A | * | 2/1983 | Colbert .................... A61C 7/12 433/18 |
| 4,511,331 | A | | 4/1985 | Scebold et al. |
| 4,725,229 | A | * | 2/1988 | Miller ............................. 433/11 |
| 4,867,679 | A | * | 9/1989 | Rackley ................... A61C 7/12 132/321 |
| 5,269,681 | A | | 12/1993 | Degnan |

(Continued)

FOREIGN PATENT DOCUMENTS

BR    8600030 U    9/2007
BR    8600342 U    11/2007
(Continued)

OTHER PUBLICATIONS

Lopes, Alexandre Gallo, PCT/BR2011/000271, International Search Report mailed Sep. 5, 2011, 2 pages.

*Primary Examiner* — Cris L Rodriguez
*Assistant Examiner* — Hao D Mai
(74) *Attorney, Agent, or Firm* — Arent Fox LLP

(57) ABSTRACT

A pre-fabricated ligature with variable friction includes a ligature made of nitinol (1) with a rectangular outline similar to an "O" format, which has free ends (2) that can be deflected to meet the need for affixing of the arch wire (3) to the bracket (5), resulting in variable friction force.

4 Claims, 2 Drawing Sheets

(56) References Cited

U.S. PATENT DOCUMENTS

| | | | |
|---|---|---|---|
| 5,857,850 A | 1/1999 | Voudouris | |
| 5,931,668 A * | 8/1999 | Birkel | A61C 7/02 433/13 |
| 6,042,374 A * | 3/2000 | Farzin-Nia | A61C 7/30 433/13 |
| 6,217,321 B1 * | 4/2001 | Kanno | 433/11 |
| 6,309,214 B2 * | 10/2001 | Birkel | A61C 7/02 433/15 |
| 6,325,622 B1 * | 12/2001 | Kelly | A61C 7/30 433/10 |
| 6,818,076 B1 | 11/2004 | Farzin-Nia | |
| 8,414,292 B2 | 4/2013 | Lopes | |
| 9,339,353 B2 | 5/2016 | Voudouris | |
| 2010/0112508 A1 | 5/2010 | Lopes | |
| 2012/0040302 A1 * | 2/2012 | Rogers | A61C 7/285 433/11 |

FOREIGN PATENT DOCUMENTS

| | | |
|---|---|---|
| BR | 0603521 A | 4/2008 |
| BR | DI6804372-4 F | 10/2008 |
| BR | MU8802474-1 U2 | 7/2010 |
| BR | MU8902352-8 U2 | 6/2011 |
| BR | 20 2012 002849-8 U2 | 3/2014 |
| DE | 29924576 U1 | 11/2003 |
| FR | 2806618 A1 | 9/2001 |

\* cited by examiner

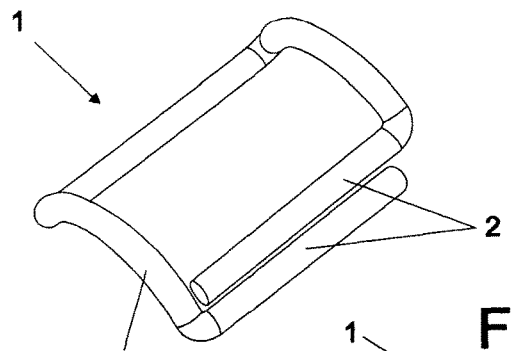
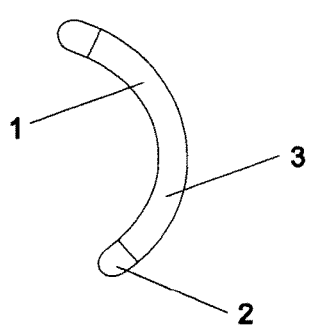
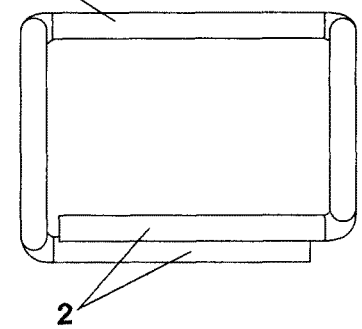
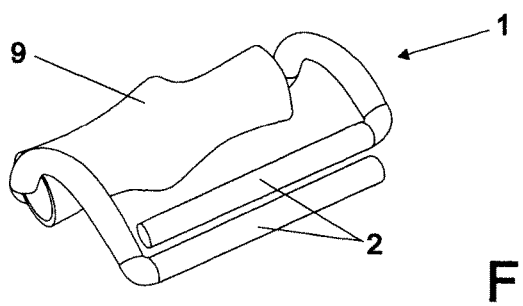
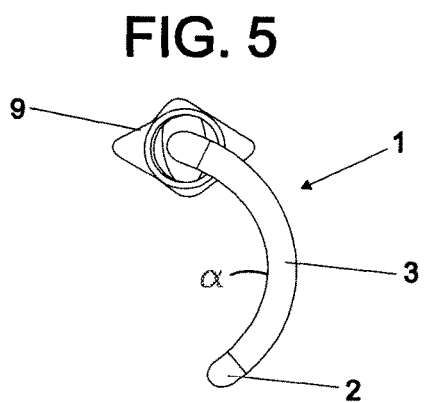
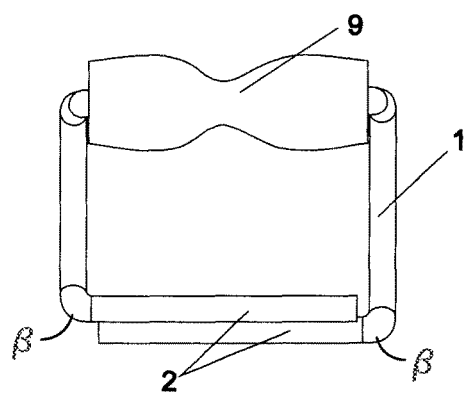

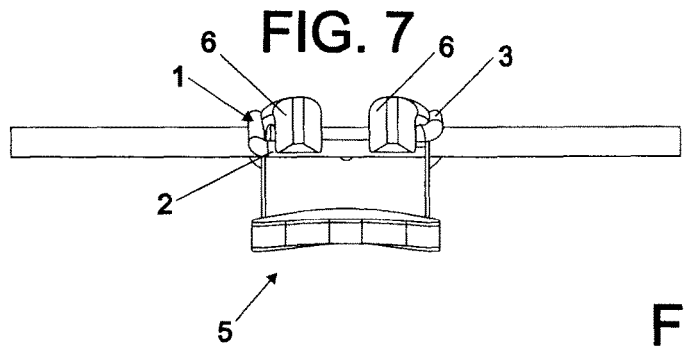
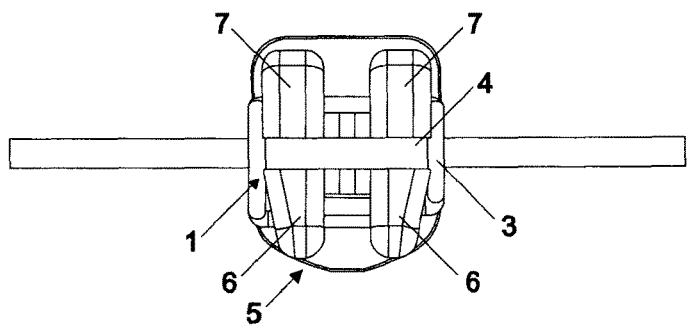
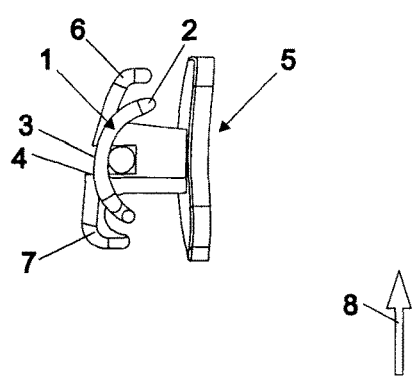
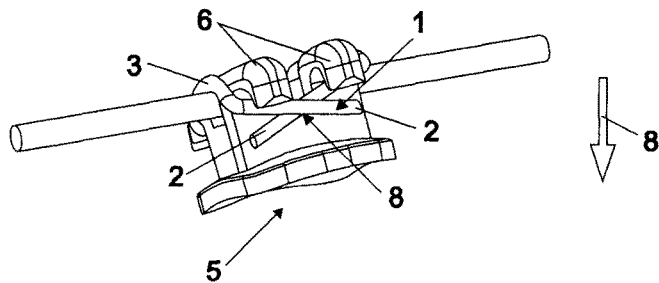
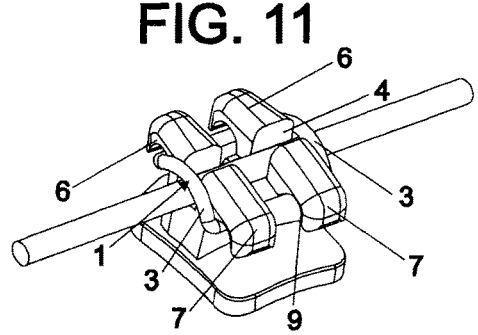
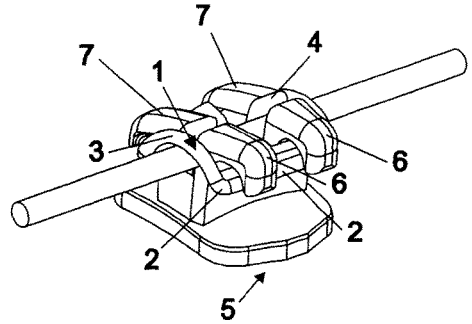

PRE-FABRICATED LIGATURE WITH VARIABLE FRICTION

CROSS-REFERENCE TO RELATED APPLICATIONS

This is a National Phase application claiming priority to PCT/BR2011/000271 filed Aug. 11, 2011, which claims priority under 35 U.S.C. §119 to MU 9001529-0 filed Aug. 11, 2010, all of which are herein incorporated by reference in their entireties.

This requirement addresses an Utility Model of the brand new pre-fabricated ligature with variable friction, notably from a biocompatible ligature in "O", pre-formed in nitinol or any other alloy with memory effect, that does not deteriorate on a mouth environment, eliminating the need for frequent exchanges, with the possibility to remain until the end of the orthodontic treatment, reducing considerably the friction cause by conventional ligatures.

Ligatures are accessories used by orthodontists or general physicians with the purpose of connecting arches of different materials to brackets that are a support for dental movement. Ligatures can be found in several different models, versions and materials. The most common ones are created by the dentists themselves in their offices, by using stainless steel wires of several calibers. For the same purpose, O-shaped elastomeric ligatures to connect arches to brackets.

Both options have limitations and disadvantages, described below:

The process of putting and removing metal and elastomeric ligatures to fasten movement arches to brackets is one of the longest and most repetitive procedures of orthodontic treatment, often causing the professional to have repetitive strain injury and increasing the treatment time spent when providing services to clients;

Metallic ligatures have to be bought in a pre-fabricated version, which is costly, or be created "in loco" by the dentist or the assistant, through the use of specific instruments, which demands time and material;

Elastomeric ligatures, in turn, deteriorate in a mouth environment, based in several studies, between 24 and 48 hours after being put there, besides from providing surfaces susceptible to plaque, harming dental health, causing friction in dental movement;

Stainless steel metallic or elastomeric ligatures cause ligature friction between arches and brackets, changing movement features, increasing the strength of arches and hiding the superelastic properties of the arches used in dental movement, dissipating the work energy of the arch deflection in friction on the interface bracket x arch and/or plastic deformation, making it hard to set a standard for its application and to determine the friction generated by this method;

The ligature strength generates normal strength (90°) on the bracket x arch interface, generating significant friction when pressing the arch against the bottom of the channel with high contact charge (superior to the energy produced by the arch deflection of the arch);

If the ligature method does not pressure the arch inside the channel towards its bottom continuously, the teeth alignment and leveling can be compromised;

Both the metallic ligature and the elastomeric ligature need to be changes when going to the dentist;

Both the metallic ligature and the elastomeric ligature lose their capacity of retention in a short period of time after its application, changing the position of the arch in relation to the channel, compromising the control of the dental movement; this problem is solved by changing the elastomeric ligatures frequently;

Both the metallic ligature and the elastomeric ligature produce an initial highly elevation retention of friction, masking the superelastic properties of the movement arches and, where the ligature strength is reduced, the strength module contained in the arch deflection is liberated and transmitted to the bracket/arch set and, consequently, to the teeth, all at once, with negative impact on the periodontal system or teeth support structures (the initial high strength can crease or create permanent deformations on the arches).

In the current state of the technique, there are several patent documents that confirm the inconveniences mentioned above, such as KR20090078229—KR100767443—JP2004329912—DE100113818—FR2773466—JP10080433—U.S. Pat. No. 5,746,592—U.S. Pat. No. 5,269,681—JP4166147.

Aware of the state of the technique, its flaws and limitations, the inventor, active in the segment, crated the pre-fabricated ligature with variable friction, able to meet the needs of the orthodontic treatment, preferably manufactured in nitinol, O-shaped, with ends that are open and free to move in the three Cartesian planes, that gives the variable friction ligature more deflection amplitude, making it easier to align and level teeth, preventing side effects on the output of movement strength and higher rotational control, significantly reducing the resistance to sliding when compared with metallic ligatures or elastomeric ligatures.

The material to be used when manufacturing the ligature claimed here is, preferably, nitinol (Nickel and Titanium alloy), that favors the maintenance of the mechanic memory and the superelastic peculiarities that ensure the adaptation to the bracket body and in eventual deflections in the movement arches.

In the Ni—Ti alloys, other elements can also be aggregated, such as, Cu, Fe, V, Co, ta, Zr and Mo. Usually, brackets are manufactures in stainless steel, but also in ceramics, plastic or compound, which does not prevent the use of the variable friction ligature.

The net ligature can be manufactured in wires that go from caliber .008" increments of .001 until caliber .002", O-shaped, with overlapped and open ends. The wires are put in different temper processes in order to give the rings a martensitic or austenitic structure, according to the use and/or phase of the orthodontic treatment. In turn, the perimeter dimensions of the ligatures can vary, in order to adapt to different bracket sizes.

In summary, the innovated variable friction ligature has the following as its most prevalent advantages:

The possibility for the conversion of conventional brackets into passive or active autoconnected brackets, depending on the interaction of the arch's wire caliber with these ligatures, enabling a low or variable friction mechanic, according to the needs of the case;

Nitinol is biocompatible, making hygiene and the maintenance of oral health easier;

Provides continuous strength and it is light enough to keep the movement arch pressed toward the bottom of the channel;

The deflection of the open and free ends under the blades of the brackets increases significantly the control of the teeth rotation, minimizing the ligature friction cause by the deflection of the segments of movement arches;

The strength of the variable friction ligature when deflecting the arch is light enough for keeping control of the movement without causing plastic deformation on the arch itself;

It does not increase the buccolingual dimension (or height) of the brackets, an advantage for the client's comfort when adapting to using the bracket, besides from reducing occlusal interference, commons in self-connecting brackets, cause by the increase of the buccolingual dimension of the bracket's body (to accommodate the opening and closing mechanism of the channels);

Improvement in relation to the material fatigue;

It allows replacement in case it breaks or in case of loss, without any impact in the cost of the treatment or in the client's safety;

Low cost, easy application and handling and eliminates the need for specific instruments or devices; the ones from the office are enough.

Below, the innovation will be explained with reference to enclosed drawings, in which are represented in an illustrative, but not limited form:

FIG. 1 shows a perspective view of the pre-fabricated ligature with variable friction;

FIG. 2 shows a side view of the pre-fabricated ligature with variable friction;

FIG. 3 shows a front view of the pre-fabricated ligature with variable friction;

FIG. 4 shows a perspective view of the pre-fabricated ligature with variable friction, with tube pressed in one section;

FIG. 5 shows a side view of the pre-fabricated ligature with variable friction, with tube pressed in one section;

FIG. 6 shows a front view of the pre-fabricated ligature with variable friction, with tube pressed in one section;

FIG. 7 shows a bottom view showing a bracket with an innovative ligature;

FIG. 8 shows a front view showing a bracket with an innovative ligature;

FIG. 9 shows a side view showing a bracket with an innovative ligature;

FIG. 10 shows a bottom perspective view showing a bracket with an innovative ligature;

FIG. 11 shows a top perspective view showing a bracket with an innovative ligature;

FIG. 12 shows a perspective view showing a bracket with an innovative ligature with a tube;

The pre-fabricated ligature with variable friction, object of this Utility Model request is a ligature manufactured in nitinol (1), with a rectangular outline, such as an O shape, that is different due to its free ends (2) able to deflect, adapting the need for fixation of the arch wire (3) to the bracket (5), changing into a variable friction force.

More particularly, the claimed ligature (1) preferably made of nitinol wire conforms a substantially rectangular outline with free ends, overlapped ends (2) that, when deflectioning, assigns a pressure that enables the variable friction of the arch wire (3) in relation to the channel (4), according to the fixation requirements. Besides, the ligature (1) has appropriate side angle ($\alpha$) to meet the arch wire outline (3) that is already inserted in the channel (4) of the bracket (5). Thus, the ligature (01) can be put under the blades (6 and 7) and around the perimeter of the bracket body (05), in which free ends (2) remain under the top blades (6), involving and keeping the dental movement arch wire segment (3) inside the channel (4). In this arrangement, an articulation ($\beta$) is created, that can make a conventional bracket into an active or passive autoconnected bracket, depending on the configuration and the geometry of the ligature (1) and of the caliber of the wire used. Therefore, with the ligature (1) positioned on the arch wire (3), inside the channel (4), the free ends (2), when deflecting, generate a moment of equal and opposite forces (8) that cause the said free ends (2) to move, pressuring the arch wire (3) just as needed.

In a constructive variation, the ligature (1) has a pressed tube (9) in a central section that is placed under the top blades (7) of the bracket (5). The tube (9) can be replaced by a part made of biocompatible, turned, microcast, sintered material, by extrusion or stamping.

What is claimed:

1. An orthodontic bracket system comprising:
    a bracket body comprising an archwire slot for receiving an archwire, a bonding base, a pair of first tie wings, and a pair of second tie wings, the archwire slot extending in an archwire slot direction; and
    a nitinol ligature configured to secure the archwire in the archwire slot,
    wherein the nitinol ligature forms a rectangular outer shape comprising two overlapping proximal parallel free ends extending in a direction parallel to the archwire slot along a first shape side, and at least one ligature portion extending over the archwire slot, wherein the portion extending over the archwire slot is non-planar, wherein the nitinol ligature does not increase the bracket system's buccolingual dimension, and wherein the two overlapping proximal parallel free ends are each free to move relative one another in a direction perpendicular to the archwire slot direction and are positioned between one of the pair of first tie wings and the bonding base.

2. The orthodontic bracket system of claim 1, wherein the nitinol ligature comprises a tube opposite the two overlapping proximal parallel free ends.

3. The orthodontic bracket system of claim 2, wherein the tube comprises a biocompatible, turned, microcast, sintered material.

4. An orthodontic bracket system comprising:
    a bracket body comprising an archwire slot for receiving an archwire, a bonding base, a pair of first tie wings, and a pair of second tie wings, the archwire slot extending in an archwire slot direction; and
    a nitinol ligature configured to secure the archwire in the archwire slot,
    wherein the nitinol ligature forms a rectangular outer shape comprising two overlapping proximal approximately parallel free ends extending in a direction approximately parallel to the archwire slot along a first shape side, and at least one ligature portion extending over the archwire slot, wherein the portion extending over the archwire slot is non-planar, wherein the nitinol ligature does not increase the bracket system's buccolingual dimension, and wherein the two overlapping proximal approximately parallel free ends are each free to move relative one another in a direction approximately perpendicular to the archwire slot direction and are positioned between one of the pair of first tie wings and the bonding base.

* * * * *